United States Patent [19]

Wyatt et al.

[11] Patent Number: 4,907,884
[45] Date of Patent: Mar. 13, 1990

[54] SAMPLE CELL MONITORING SYSTEM

[75] Inventors: Philip J. Wyatt, Santa Barbara; Steven D. Phillips, Goleta, both of Calif.

[73] Assignee: Wyatt Technology Corporation, Santa Barbara, Calif.

[21] Appl. No.: 59,157

[22] Filed: Jun. 5, 1987

Related U.S. Application Data

[60] Continuation of Ser. No. 861,863, May 12, 1986, abandoned, which is a division of Ser. No. 671,181, Nov. 15, 1985, Pat. No. 4,616,927.

[51] Int. Cl.[4] ............................................. G01N 15/02
[52] U.S. Cl. ..................................... 356/336; 356/343
[58] Field of Search ............... 356/336, 337, 338, 339, 356/340, 341, 342, 343; 250/564, 565

[56] References Cited

U.S. PATENT DOCUMENTS

| | | | |
|---|---|---|---|
| 3,713,743 | 1/1973 | Simms | 356/338 |
| 4,134,679 | 1/1979 | Wertheimer | 356/336 |
| 4,167,335 | 9/1979 | Williams | 356/336 |
| 4,515,473 | 5/1985 | Mermelstein | 356/33 |
| 4,541,719 | 9/1985 | Wyatt | 356/343 |

OTHER PUBLICATIONS

Arkin et al., *Statistical Methods*, Barnes & Noble, Inc., New York, fifth edition, copyright 1970, pp. 29–30.

*Primary Examiner*—Richard A. Rosenberger
*Attorney, Agent, or Firm*—Philip J. Wyatt

[57] ABSTRACT

The light intensity incident on a scattering sample contained in a scattering cell is monitored by simultaneous measurements of the light incident on the cell before entering it and the light transmitted through the cell after leaving it. Means to monitor the product of these signals is disclosed and how this product is related to the actual incident intensity at the sample is explained. The invention is presented in the context of the scattering cell of the parent application.

12 Claims, 5 Drawing Sheets

SAMPLE CELL MONITORING SYSTEM

Some of the developments and studies associated with this invention were performed under Contract #DAMD17-84-C-4155 from the U.S. Army Medical Research and Development Command. The Government has certain non-exclusive rights under the terms of this contract.

This is a continuation of application Ser. No. 861,863, filed May 12, 1986, now abandoned, which is a division of application Ser. No. 671,181, filed Nov. 15, 1985, now U.S. Pat. No. 4,616,927.

The present invention concerns a new technique for monitoring the intensity of light directly incident on a scattering sample and correcting for both reflection losses and attenuation by the sample itself.

As such it will find broad utility in various fields of light scattering determinations. Among some of the most important are those of the type discussed at length in the following patents and co-pending application by one of the inventors of the monitoring technique, namely:

U.S. Pat. No. 4,490,042
  Title: Method for Determining the Properties of Wine
  Inventor: Philip J. Wyatt
  Filing Date: June 4, 1981
    Issue Date: Dec. 25, 1984
    Art Unit No.: 257
U.S. Pat. No. 4,548,500
  Title: Process and Apparatus for Identifying or Characterizing Small Particles
  Inventors: Philip J. Wyatt and Gregory M. Quist
  Filing Date: June 22, 1982
    Issue Date: Oct. 22, 1985
    Art Unit No.: 255
U.S. Pat. No. 4,541,719
  Title: Method and Apparatus for Characterizing Microparticles and Measuring Their Response to Their Environment
  Inventor: Philip J. Wyatt
  Filing Date: July 20, 1982
    Issue Date: Sept. 17, 1985
    Art Unit No.: 255
U.S. patent application Ser. No. 668,711
  Title: Method and Apparatus for Measuring the Light Scattering Properties of Small Particles
  Inventors: Philip J. Wyatt and Steven D. Phillips
  Submis. Date: Nov. 5, 1984

DEFINITIONS

The term "light" shall mean electromagnetic radiation, either monochromatic or of a broader frequency range, either unpolarized or polarized.

The term "size parameter" shall mean $\rho$, where $\rho = 2\pi a/\lambda$, a is the mean particle radius, and $\lambda$ is the wavelength of the incident electromagnetic radiation in the medium in which the particles are measured.

The term "small particle" shall mean any particle whose size parameter is less than six.

The term "large particle" shall mean a particle whose size parameter is greater than six.

The term "beam" shall mean light propagating in a parallel or nearly parallel direction.

The term "beam diameter" of an incident light source, with a Gaussian intensity profile, such as a laser, shall refer to the diameter of the beam measured between the points at which the intensity has fallen to $1/e^2$ the intensity at the center of the beam.

The term "forward scattering direction" shall mean all rays, i.e. directed line segments, propagating at an angle less than 90 degrees with respect to the direction of the incident beam.

The term "backward scattering direction" shall mean all rays, i.e. directed line segments, propagating at an angle greater than 90 degrees with respect to the direction of the incident beam.

For plane polarized light, the plane perpendicular to the direction of the wave's electric field is called the V-plane and said plane polarized light is vertically polarized with respect to said perpendicular plane. The corresponding H-plane is perpendicular to the V-plane and contains the incident wave's electric field.

The terms "background effects" and "background contributions" shall mean any source of light detected by an instrument which is not due to the scattering of light from the sample. We will be concerned solely with background contributions arising from interactions of the incident beam with the sample cell and related apparatus. We will assume any background produced by light scattering from a pure solvent itself is negligible.

SUMMARY OF THE INVENTION

This invention is concerned with a new means for monitoring the intensity of light incident upon a scattering source so that the scattered light intensities recorded therefrom may be normalized accurately to the radiation flux incident thereon. The monitoring of the incident light source is achieved by means of two detectors; one monitors a fraction of the incident light *before* it enters the cell and the second monitors the light *after* it traverses and emerges from the cell. The square root of the product of these two values is then used to normalize each detected scattered signal by the light incident on the scattering sample by dividing each such detected scattered signal by said square root value. In the detailed description of this invention, the square root of the product of these two measurements is shown to be proportional to the incident intensity at the sample. The monitoring invention is further disclosed in the context of the new flow cell of the parent application.

BACKGROUND

Many important laboratory and industrial programs are involved with the measurement of fine particles in suspension by light scattering techniques. Foremost among them is the light scattering procedure for the determination of molecular weights of unknown solutes suspended in various types of solvents. Without going into the details of this procedure, which is described in many texts such as Kerker's book *The Scattering of Light and Other Electromagnetic Radiation*, the general measurement involves the preparation of a suspension of the unknown material followed by its illumination by a collimated beam of monochromatic light. The intensity of the light scattered by the suspension is then measured as a function of angle and solute concentration. Since the scattering properties of the sample cell or cuvette containing the solution may interfere with this determination, it is important to use a cell whose so-called "background" contributions will be minimal and affect the determinations least. Ideally, the cell will permit the measurement of the scattering properties of the solute particles or molecules at increasingly lower concentrations.

Many types of assays and bioassays, such as described by Wyatt in his two co-pending applications cited above or his chapter in the book edited by Charalambous entitled *Analysis of Foods and Beverages*, involve the preparation of aqueous suspensions. Subsequent measurement of these suspensions by light scattering means involves detecting very small changes in the measured light scattering properties of the solutions. Often, the accuracy of the results will be affected by background effects created by the scattering cell itself. Even the very simplest determinations of transmission or optical density, such as performed by conventional spectrophotometers of the type manufactured by Bausch and Lomb, depend critically on the background contributions of the liquid-containing cell. Furthermore, some compounds, such as those separated by means of liquid chromatography, are obtained in such small volumes that the cell containing them also must have a very small volume, typically on the order of microliters or less. Thus, "background" effects become increasingly important because of the close proximity of the sample cell liquid and air interfaces to the field of view of the detection system.

While studying many of the aforementioned measurements, we have discovered a cell structure and method of measurement that permits the examination by light scattering means of extremely small volumes of liquid-borne samples at virtually all scattering angles, no matter how small, without introducing significant background artifacts from the containing sample cell itself. This cell structure permits, in addition, the determination of the actual light flux incident upon the sample being examined, an often important requirement for many light scattering applications.

DETAILS OF THE INVENTION

Figure 1:
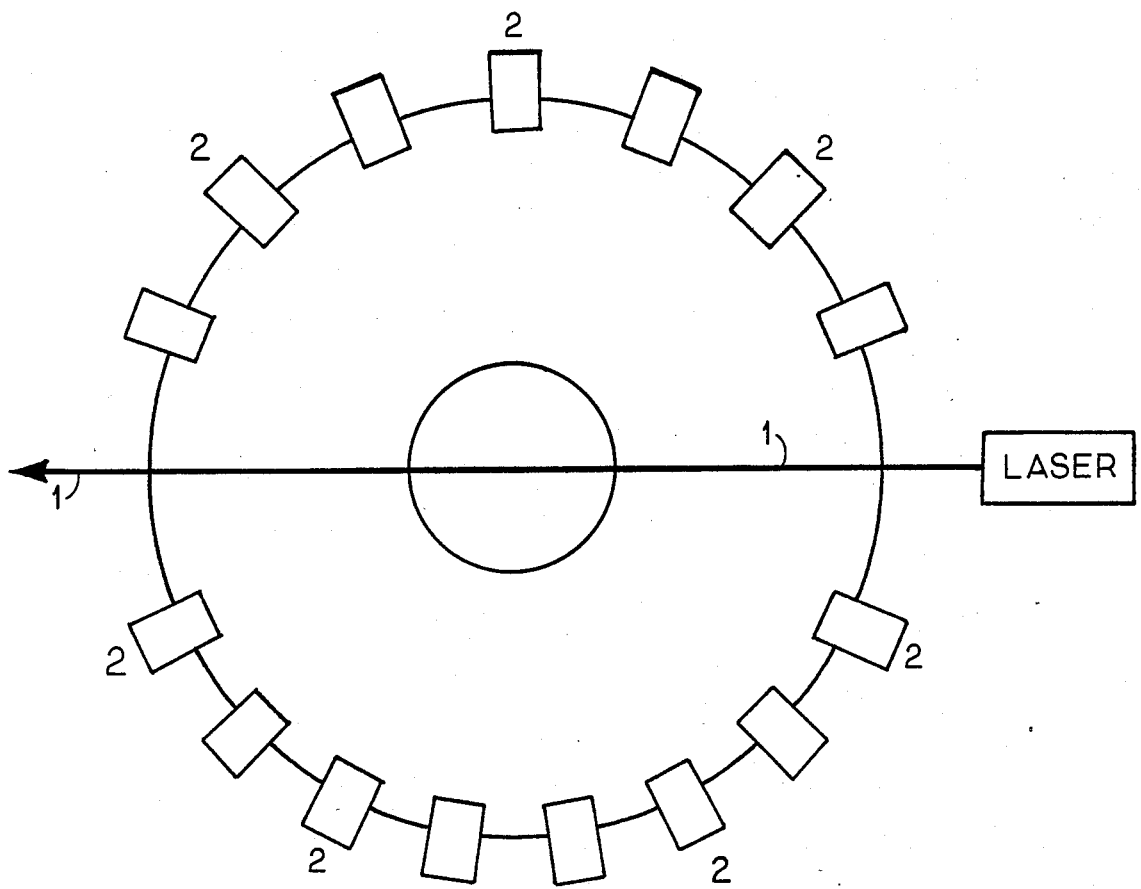
FIG. 1 shows a top view of a cylindrical scattering cell surrounded by a set of collimated detectors and illuminated by a collimated light beam.

A typical detection system is shown in FIG. 1. An incident light source, usually a monochromatic beam 1 such as produced by a laser passes through the sample cell. Also shown in this figure is a set of discrete detectors 2 spaced circumferentially about this cell. Each detector is collimated so that its field of view includes only a very small volume at the center of the cell.

Figure 2:
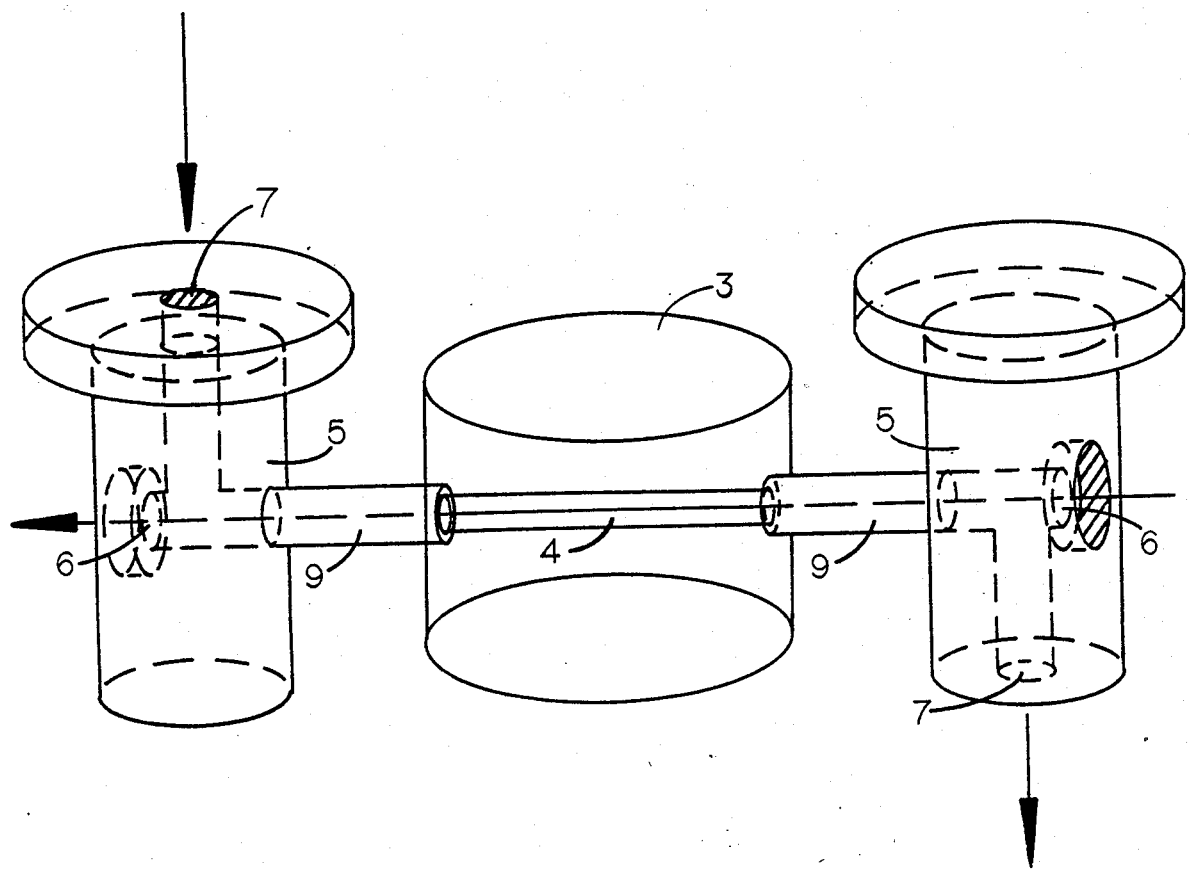
FIG. 2 presents a perspective view of a preferred embodiment of the scattering cell showing the illumination source, the flow channel, the cell windows, and the fittings for introducing samples.

FIG. 2 presents a perspective view of the scattering cell of the preferred embodiment of our invention. It consists of a cylinder 3 of glass or other transparent material of refractive index generally chosen close to the index of the solvent carrying the sample. Through the cylinder, a hole 4 is drilled along a diameter of the cylinder and lying in the plane of the detector array. The outer diameter of the cylinder and the hole interior surfaces are optically polished to remove any surface irregularities. Attached to each aperture of the cylinder is a fixture 5 containing an optical window 6 and a bore 7 to carry the sample into or out of the cell.

Figure 3:
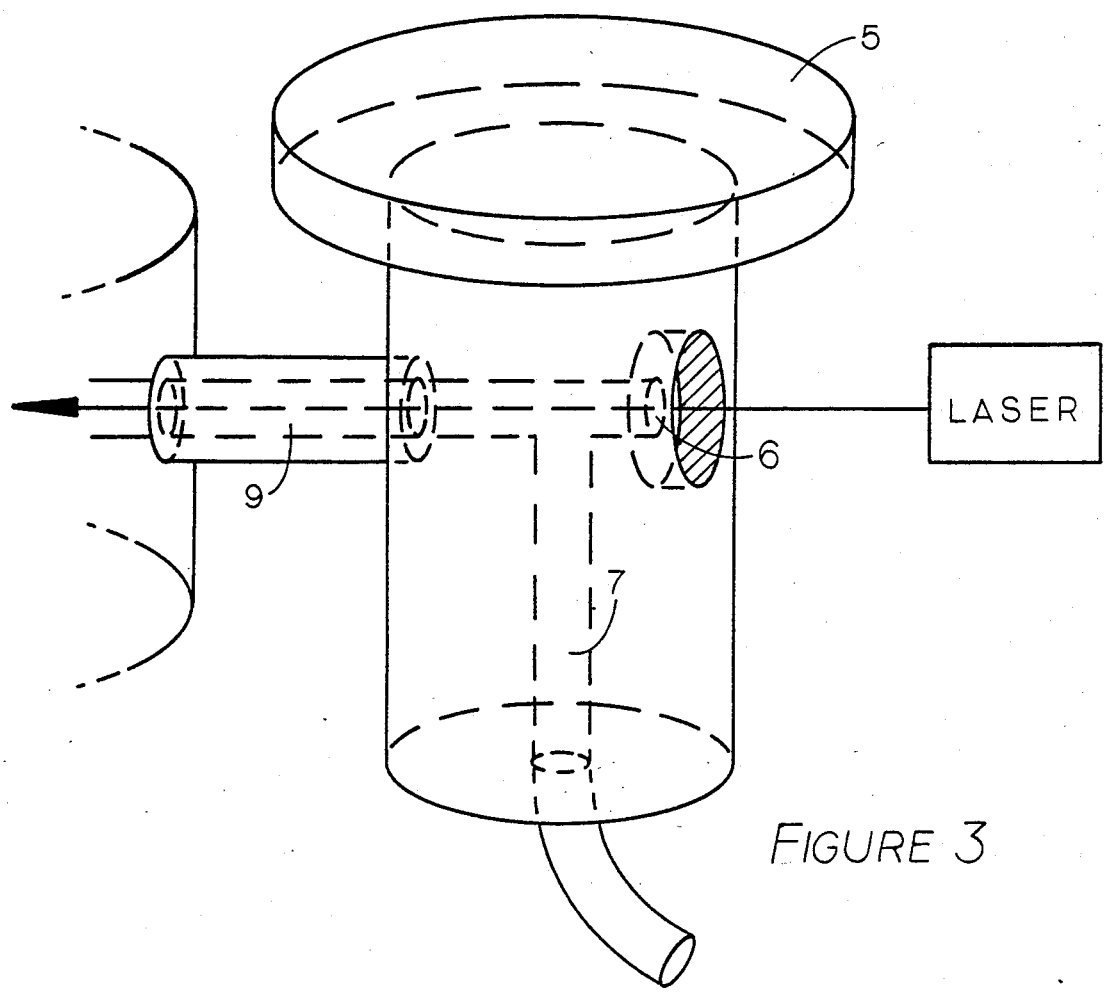
FIG. 3 shows a flow fixture that is attached to the cylindrical sample cell to carry liquid-borne samples into or out of it.

FIG. 3 shows a greater detail of the fixtures 5 which, in the preferred embodiment of this invention, contains a tube 9 to convey the liquid-borne sample into or out of the cell hole 4. Note that the light beam that passes through the cell must, in the preferred embodiment of this invention, be of even smaller cross section than the hole 4. A typical cell would have a hole diameter of 2.0 mm and be illuminated with a laser beam diameter of 0.4 mm such as is produced by a special He-Ne laser manufactured by Melles Griot. As should be evident from FIGS. 1-3, were the refractive index of the cylinder the same as the refractive index of the liquid passing through the cell, the set-up would correspond to the geometry of the large radius of curvature structure of FIG. 1; yet the beam passing through the cell of the present invention does not strike any surface within the field of view of any detector. As seen in FIG. 2, the beam entrance and exit windows 6 are far removed from the center of the cell, which eliminates the background contributions associated with the beam traversing an air/glass/liquid interface. In addition, the sample volume contained within this cell is extremely small relative to the volume required for the traditional cell of such large radius of curvature. The actual volume of the sample would depend on the diameter of the hole 4 cut into the cylinder. Light scattered from this small sample volume will not be attenuated significantly as it passes through the glass cell region to the detectors. This also permits the examination of samples of greater particle density without the usual multiple scattering degradations that would be caused by the intervening particles in a comparably sized scattering cell, i.e. a cell where the glass region of the present invention were replaced by an additional liquid sample.

The difference of refractive index between the solvent fluid passing through hole 4 and that of the glass cylindrical cell 3 surrounding it results in another important feature of our invention. We have already stated that these refractive indices will be quite close. As long as they are different, it will be possible to obtain measurements of light scattered at very small angles by particles or molecules illuminated by the highly collimated light source with negligible background contributions, as shall soon be demonstrated. Typically, the refractive index of the liquid $n_1$ will be that of water, 4/3, while that of the glass $n_2$ will be about 3/2. Applying Snell's Law (see FIG. 4) to determine the refraction of a ray 1 striking the water-glass interface 8 at an angle $\theta$ yields the result $$n_1 \sin(\pi/2 - \theta) = n_2 \sin(\pi/2 - \theta') \tag{1}$$

where the angle of incidence is $\pi/2 - \theta$ and the angle of refraction is $\pi/2 - \theta'$. Expanding the sine functions in Eq. (1) and collecting terms, immediately results in $$n_2 \cos\theta' = n_1 \cos\theta, \tag{2}$$

Note that point 9, for the case of the scattering cell of the preferred embodiment, lies ahead, i.e. to the left, of the center of the cell 10, and is on the interface. A detector means detecting light at an angle $\theta'$ would be collimated to be centered on point 10.

It is interesting to note that as the scattering angle $\theta$ becomes very small, i.e. approaches zero, the source of the scattering event 11 whose refracted rays are detected at $\theta$ moves to the right of the center of the cell 10. In the limit at $\theta=0$, $\theta'=\cos^{-1}(8/9)=27.27°$. Thus, no matter how small the scattering angle $\theta$, the refracted ray will be detected at an angle $\theta'$ sufficiently distant from all interfaces to permit said detector means to avoid receiving any direct contributions from the incident beam 1.

Figure 4:
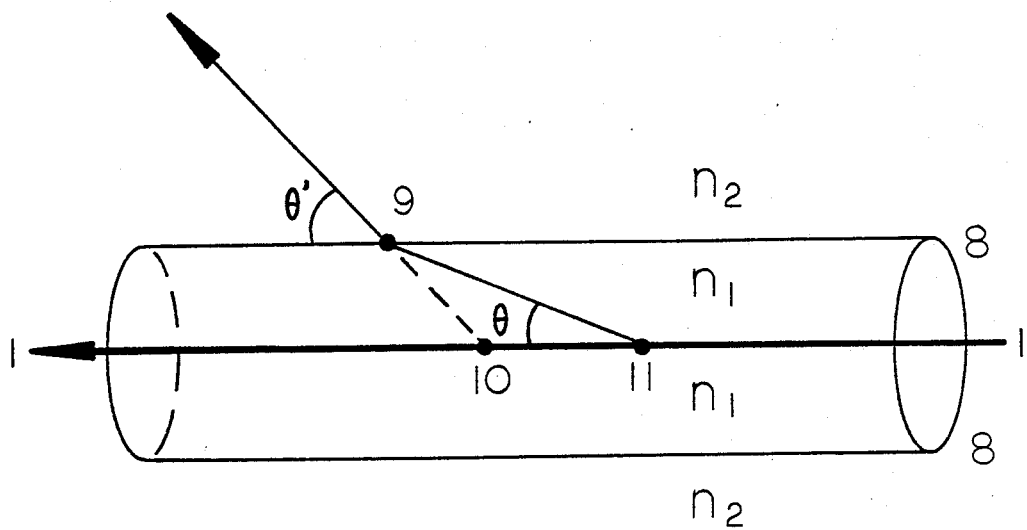
FIG. 4 shows the application of Snell's Law at the interface between two media.

The scattering angle $\theta$ of FIG. 4 represents the most important independent variable of a light scattering measurement. Accordingly, in the preferred embodiment of our invention, the detector means 2 of FIG. 1 should be placed so that there is a one-to-one correspondence with the set of $\theta$-angles selected for an experiment. An often used set of scattering angles $\theta$ is selected such that the angles are equally spaced in $\sin \theta/2$. The latter choice is particularly convenient for certain types of measurements related to molecular weight determinations or small particles whose refractive indices are very close to that of the medium surrounding them. If the detectors surrounding the glass cell were spaced equidistantly in $\theta'$ or $\sin \theta'/2$ the interpretation of the data so-detected in terms of the physical important scattering angle $\theta$ would require the complex mathematical inversion of Eq. (1) for each measurement. Instead, in a preferred embodiment of our invention, we place the detector means about the cell at those angles $\theta'$ that correspond to the selected set of scattering angles $\theta$. For example, for equidistant spacing in $\sin \theta/2$ such that $$0.2 \leq \sin \theta/2 \leq 0.9, \tag{3}$$

which is a range frequently found in scattering measurements, Eq. (1) may be solved for $\theta'$ in terms of $\sin \theta/2$ as follows:

$$n_2 \cos \theta' = n_1 \cos \theta = n_1 (1 - 2 \sin^2 \theta/2). \tag{4}$$

$$\text{Hence } \theta' = \cos^{-1}\left[\frac{n_1}{n_2}(1 - 2 \sin^2 \theta/2)\right]. \tag{5}$$

For a typical case where the cell is optical glass of refractive index 3/2 and the sample is in a liquid of refractive index 4/3, a set of detectors at angle $\theta$ would be placed according to the transformation table below:

| Table of Transformed Scattering Angles | | |
|---|---|---|
| $\sin\theta/2$ | $\theta$ | $\theta'$ |
| .2 | 23.07 | 35.13 |
| .25 | 28.96 | 38.95 |
| .3 | 34.92 | 43.21 |
| .35 | 40.97 | 47.84 |
| .4 | 47.16 | 52.81 |
| .45 | 53.49 | 58.07 |
| .5 | 60.00 | 63.61 |
| .55 | 66.73 | 69.44 |
| .6 | 73.74 | 75.59 |
| .65 | 81.08 | 82.08 |
| .7 | 88.85 | 88.98 |
| .75 | 97.18 | 96.38 |
| .8 | 106.26 | 104.41 |
| .85 | 116.42 | 113.30 |
| .9 | 128.32 | 123.45 |

To make a measurement at a very small scattering angle in the forward direction will require a very precise placement and collimation of the detector means, since refraction causes a small range of $\theta'$ values to correspond to a larger range of $\theta$-values for $\theta$ near 0°. For a measurement at, say, $\theta=5.73°$, the detector means would have to be placed at 27.82°, a scant 30' of arc from the limiting $\theta=0°$ value, where $\theta'=27.82°$. Nevertheless, light scattered in this direction may be precisely intercepted by the carefully set detector means.

As the average particle size parameter $\rho$ becomes larger, the relative intensity of light scattered in the forward direction to that scattered into the backward direction becomes very large. For many types of instruments detecting scattered light at small angles, this becomes a troublesome problem as large forward scattering contributions may overwhelm and saturate the detector means monitoring forward scattering events. This is not true for our invention because of the unique attenuation of such forward scattered light. As $\theta \to 0$, the fraction of scattered light flux refracting into angle $\theta'$ becomes progressively smaller and becomes zero when $\theta=0$. In FIG. 4, the fraction of scattered light flux reflected at the water glass interface 8 in terms of the angle of incidence, $\theta$, may be determined from Fresnel's relations discussed, for example, in the textbook *Light* by R. W. Ditchburn. For the case of vertically polarized incident light, the reflected fraction $\rho_w$ from liquid to glass is given by the relation $$\rho_w = \frac{\tan^2(\theta' - \theta)}{\tan^2(\theta' + \theta)} \tag{6}$$

where $\theta$ is given by Eq. (2). Note that as $\theta \to 0$, $\rho_w \to 1$, i.e. most of the light is reflected and only a decreasing fraction $1 - \rho_w$ is transmitted to the small angle detector means. In the case or normal incidence $\theta$ and $\theta' \to \pi/2$. Taking this limiting case and applying Snell's law, we obtain $$\rho_{w90°} = (n_1 - n_2)^2/(n_1 + n_2)^2 = (1/6)^2/(17/6)^2 = 0.34\%$$

Thus by placing the scattering particles in a medium of refractive index *less* than that of the surrounding scattering cell, which is a natural procedure whenever particles are measured in solution, our invention permits the detection of light scattered at small angles without saturating the small angle detector means.

Although we have explained the key elements of our invention by means of a preferred cylindrical embodiment discussed above, it will be clear to those skilled in the art of light scattering that our invention applies equally to many other geometries and cell structures. The latter is of particular significance as it represents the hydrosol equivalent of the single particle aerosol particle analyser disclosed in the patent of Wyatt and Phillips. Highly irregular particles will scatter light as a complex function of both the polar angle $\theta$ and the azimuthal angle $\phi$. The variation of intensity with $\phi$ at a fixed $\theta$ or a spherically symmetric particle, on the other hand, is a simple function of $\cos^2\phi$ and $\sin^2\phi$. The detection, classification, and measurement of particles of complex structure requires, therefore, that measurements be performed at many $(\theta, \phi)$ locations that do not lie in a plane. If the incident light be plane polarized vertically with respect to a set of detectors lying along a great circle of the sphere/air interface, then there is another great circle at right angles to this with respect to which the incident light is horizontally polarized. Further details of the detection geometries are discussed in the cited Wyatt and Phillips' patent. The measurement and classification of such particles from the collected light scattering data are discussed in the patent of Wyatt and Quist. Note also that a sphere is not the only three dimensional structure for which our invention will apply, though it certainly provides the greatest flexibility for scattering measurements. Other useful three dimensional structures include cubes and many regular and irregular polyhedra.

It is interesting to note that the transformed detector locations discussed above for the cylindrical cell embodiment of our invention apply equally well to a spherical cell. The angle of incidence of the scattered ray depends only on $\theta$ insofar as the application of Snell's law is concerned and is independent of $\phi$. The azimuthal scattering angles $\phi$ would be selected to define different sets of detectors, each lying on a great circle, as described by Wyatt and Phillips.

It should be noted that the hole 4 through the cell can contain additional structures such as a small spherical cavity at the center of the cell. This cavity would allow scattered light originating at the center of the cell to proceed along a radial line out of the cell and into the detectors. This would eliminate the refraction problem at the liquid/glass interface arising from the non-perpendicularity of the scattered ray at the interface. Hence, all detectors, except those whose field of view is obscured by hole 4, will be simultaneously viewing the center of the cavity. Such an arrangement would be important when, for example, viewing a single particle is desired, which requires many detectors viewing the same particle at the same location at the same time. The spherical cavity within the spherical cell could be easily fabricated, for example, by assembling the spherical cell from two hemispheres ground on a lens grinding machine. After cutting a sample introducting channel in each hemisphere and a central hemispherical cavity in each hemisphere, the two hemispheres and cavities would be polished and joined together by index matching cement.

Figure 5:
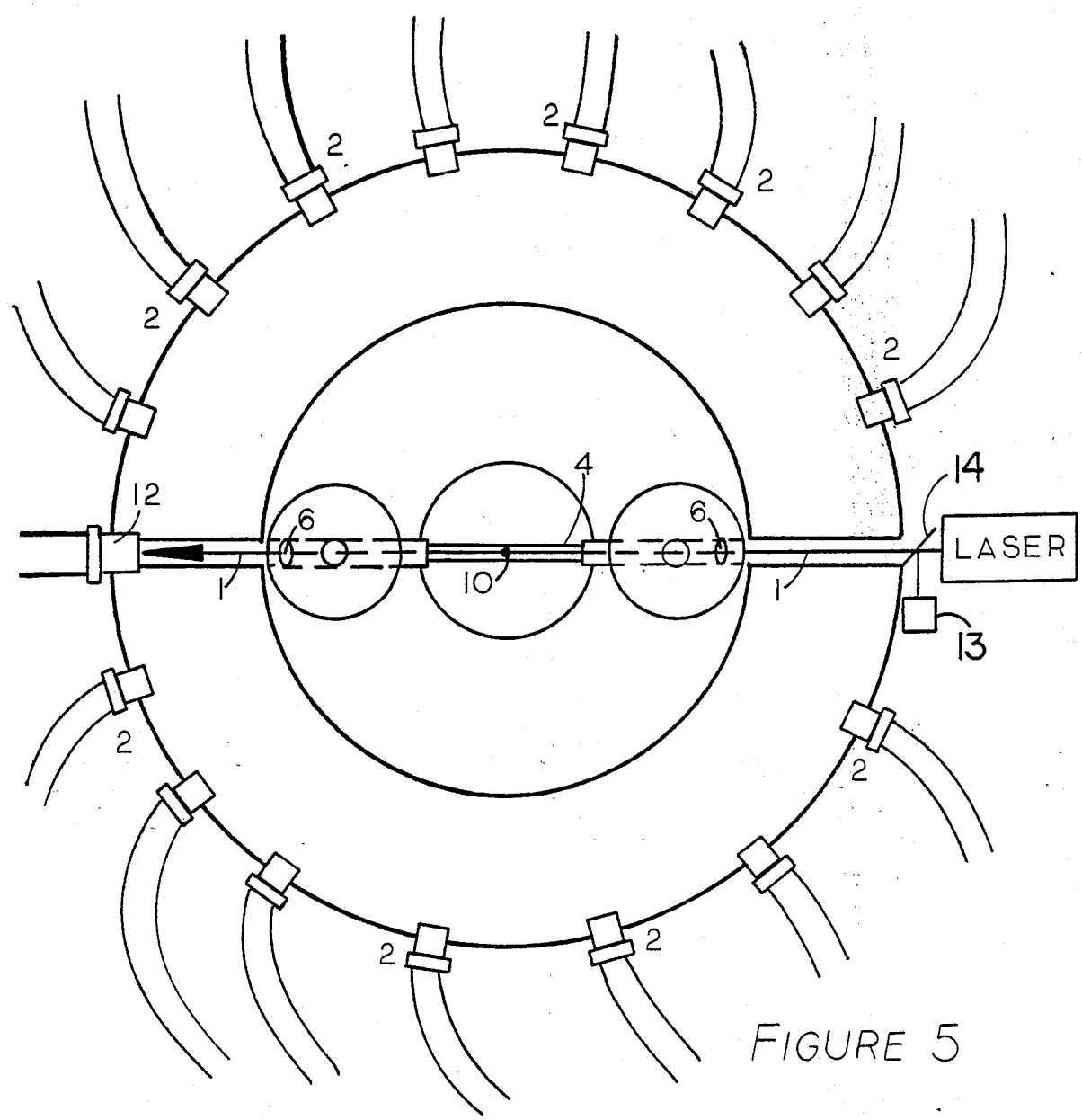
FIG. 5 is a top view of a preferred embodiment showing the sample cell, the normalization beam monitor, several typical detector means, and the illumination source with its monitor.

FIG. 5 shows a perspective view of the assembled cell complete with fixtures and surrounded with an array of detectors. A source monitor 13 monitors a fraction K of the incident source. A traditional form of such a monitor is based on a beam (14) splitter that would split off some fraction of the source beam before it enters the scattering cell. Other source monitoring configurations may be suitably employed as long as they monitor a fraction of the light source itself and are directly proportional thereto. Consider the beam monitor 12. It will monitor the beam intensity after passing through the sample. If n is the number of particles per ml and $\sigma$ is the average scattering cross section per particle, then in a path length X, the intensity I of the illumination source will be attenuated according to Beer's Law as:

$$I = I_o \exp-(n\sigma X), \tag{8}$$

where, $I_o$ = the incident intensity. For many types of measurements, it is important that the scattered intensities detected be normalized to the intensity of the illumination incident upon the scattering particles. This normalization is particularly important in the measurement of molecular weights or monitoring critical growth processes. Some instruments split the incident beam and use the fraction removed thereby as this normalization factor $I_o$. However, this value, so-obtained, may not well represent the actual intensity at the sample because of the attenuation of the intervening sample and reflections at the cell interfaces. Furthermore, this attenuation will vary from sample to sample. By introducing a beam monitor such as shown in FIG. 5, we are able to obtain very accurate representations of the normalized scattered intensities as follows.

Consider that the total sample path through the cell hole 4 is 2X and that the detectors 2 are collimated to view only the small volume at the center of the hole, a distance X from the beam entrance window 6 in FIG. 5. The intensity at the beam monitor 12 relative to the incident intensity at the entrance window is given by application of Beer's Law with the incorporation of the Fresnel reflection fraction f, at each air-glass interface and Fresnel reflection fraction g at each glass/liquid interface. Hence the total reflection fraction is $F = f + g - fg$ whence:

$$I_2 = I_o(1-F)^2 \exp-(2n\sigma X). \tag{9}$$

The intensity at the center of the sample, $I_1$, on the other hand, is just $$I_2 = I_o(1-F) \exp-(n\sigma X). \tag{10}$$

Instead of normalizing the scattered intensities by $I_o$, we should normalize by the factor of $I_1$ of Eq. (10). However, the normalization factor $$N = I_1 = I_0 (1 - F)\exp - (n\sigma X), \tag{11}$$

$$= \sqrt{I_0} \ \sqrt{I_2}$$

Furthermore, any normalization factor which is proportional to N is an equally suitable normalization factor. We are only concerned with the relative intensity at the center of the cell which varies from sample-to-sample due to differences in turbidities and from time-to-time due to the time varying intensity of the light source.

$$\text{Let } N_2 = \sqrt{I_3} \ \sqrt{I_2} \tag{12}$$

where $I_3 = K I_0, 0 < K < 1$

Hence, by monitoring a small fraction, K, of the incident source intensity at the external source monitor 13 and monitoring $I_2$ at the beam monitor 12, one obtains $N_2$ via Eq. (12). The value of K need not be known as $N_2$ is only a relative normalization factor.

This final normalization obtained as the square root of the product of relative intensities at the beam monitor 12 and an external monitor 13 represents, therefore, the optimum normalization constant since it is always proportional to the real time value at the sample.

While there has hereinbefore been presented what is at present considered to be the preferred embodiment and process of our invention which has described a technique for measuring the scattered light intensities from small particles and molecules in solution over a broad range of scattering angles including those near zero degrees, it will be apparent to those of ordinary skill in the art of light scattering that many modifications and variations may be made therefrom without departing from the true spirit and scope of the inven-

What is claimed is:

1. A method for normalizing the scattered intensities of light from particles suspended in a solvent and illuminated by a collimated light beam comprising the steps of
   A. Measuring the intensity of light transmitted undeviated through the sample and external to the sample containing cell, $I_s$;
   B. Measuring a fraction of the incident light source intensity before entering the cell, $I_f$;
   C. Dividing all measured scattering intensities at specified scattering angles by the quantity $\sqrt{I_f I_s}$, where $I_s$ is the intensity value measured in step A and $I_f$ is the intensity value measured in step B.

2. The method of claim 1 where the sample is confined to a channel and the illuminating light beam has a diameter much smaller than the diameter of the channel.

3. The method of claim 1 where the light beam is from a laser.

4. The method of claim 3 where the light from the laser is polarized.

5. The method of claim 1 where the fraction of the incident light source intensity is obtained from a beam splitter, said beam splitter dividing the incident beam into a source beam which illuminates the sample and a reference beam which illuminates the source beam monitor.

6. The method of claim 1 where the sample is contained in a cell between two transport windows and said illuminating collimated light beam passes through first transparent window means, then through said sample, and finally through second transparent window means.

7. The method of claim 6 where the medium external to each said transparent window means is air.

8. The method of claim 1 where the collimated light beam is plane polarized.

9. A sample cell monitor for generating a normalization factor by which means scattering light intensity values measured at a plurality of angles may be normalized by dividing each measured intensity by said normalizing factor, said sample cell containing a suspension of particles in a solvent solution that is illuminated by a collimated light beam that passes undeviated through the sample cell by entrance and exit window means provided therefore, and comprised of
   A. Detector means for measuring a value proportional to the incident light beam intensity before said beam enters said sample cell;
   B. Detector means for measuring a value proportional to the intensity of the light beam passing undeviated through the sample cell;
   C. Multiplication means forming a value proportional to the product of the value from said incident light beam detector means and said undeviated light beam detector means;
   D. Normalization generation means that forms normalization factor proportional to the square root of the product value of step C;
   E. Division means to divide said scattered light intensity values by said normalization factor.

10. The monitor of claim 9 where the collimated light beam is a laser.

11. The monitor of claim 10 where the light from the laser is polarized.

12. The monitor of claim 9 where the incident light beam is split by a beam splitter before the said light beam enters the sample cell and where said split component is measured by said detector means of step A.

* * * * *